US009572626B2

(12) United States Patent
Verner et al.

(10) Patent No.: US 9,572,626 B2
(45) Date of Patent: Feb. 21, 2017

(54) ACTUATED CANNULA SEAL

(71) Applicant: INTUITIVE SURGICAL OPERATIONS, INC., Sunnyvale, CA (US)

(72) Inventors: Lawton N. Verner, Santa Clara, CA (US); Stephen J. Blumenkranz, Los Altos Hills, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/181,541

(22) Filed: Feb. 14, 2014

(65) Prior Publication Data
US 2014/0236177 A1    Aug. 21, 2014

Related U.S. Application Data

(60) Provisional application No. 61/765,616, filed on Feb. 15, 2013.

(51) Int. Cl.
*A61B 19/00* (2006.01)
*A61B 17/34* (2006.01)

(52) U.S. Cl.
CPC ....... *A61B 19/2203* (2013.01); *A61B 17/3462* (2013.01); *A61B 34/30* (2016.02)

(58) Field of Classification Search
CPC .................................................... A61B 19/00
See application file for complete search history.

(56) References Cited

U.S. PATENT DOCUMENTS

| 4,895,346 A | 1/1990 | Steigerwald |
| 5,295,994 A | 3/1994 | Bonutti |
| 5,788,676 A | 8/1998 | Yoon |
| 5,997,515 A | 12/1999 | De La Torre et al. |
| 6,142,981 A | 11/2000 | Heck et al. |
| 9,295,523 B2 | 3/2016 | Blumenkranz et al. |
| 2006/0241671 A1 | 10/2006 | Greenhalgh |
| 2007/0260186 A1 | 11/2007 | Lang |
| 2008/0065111 A1* | 3/2008 | Blumenkranz .... A61B 19/2203 606/130 |
| 2008/0290605 A1 | 11/2008 | Brockmeier et al. |
| 2009/0234293 A1 | 9/2009 | Albrecht et al. |
| 2009/0240204 A1 | 9/2009 | Taylor et al. |

(Continued)

FOREIGN PATENT DOCUMENTS

WO    WO-2008109408 A2    9/2008

OTHER PUBLICATIONS

Partial supplementary Search Report for Application No. 13748661. 9, mailed on Oct. 21, 2015, 6 pages.

(Continued)

*Primary Examiner* — William Thomson
*Assistant Examiner* — Jeffrey Lipitz

(57) ABSTRACT

Embodiments of an actuated cannula seal are disclosed In some embodiments, a cannula seal includes a base portion that engages with a cannula; and a seal portion integrally formed with the base portion, the sealing portion capable of engaging with an instrument shaft, the sealing portion capable of being actuated by an actuator so that the sealing portion is continually in motion relative to the instrument shaft. The actuation of the sealing portion can be accomplished by rotation or vibration of the sealing portion relative to the instrument shaft.

45 Claims, 12 Drawing Sheets

(56) References Cited

U.S. PATENT DOCUMENTS

| | | |
|---|---|---|
| 2009/0275898 A1 | 11/2009 | Wenchell |
| 2009/0318868 A1 | 12/2009 | Racenet et al. |
| 2009/0326460 A1 | 12/2009 | Beardsley |
| 2010/0168675 A1 | 7/2010 | Cindrich et al. |
| 2010/0261969 A1* | 10/2010 | Fischvogt .......... A61B 17/3498 600/201 |
| 2011/0040255 A1 | 2/2011 | Schweitzer et al. |
| 2011/0087170 A1 | 4/2011 | Insignares et al. |
| 2011/0152788 A1 | 6/2011 | Hotter |
| 2013/0211423 A1 | 8/2013 | Blumenkranz et al. |

OTHER PUBLICATIONS

International Preliminary Report on Patentability for Application No. PCT/US2013/026519, mailed on Aug. 19, 2014, 9 pages.
International Search Report and Written Opinion for Application No. PCT/US2013/026519, mailed on Jun. 3, 2013, 14 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Non Final Office Action mailed Jul. 16, 2015 for U.S. Appl. No. 13/769,036, filed Feb. 15, 2013, 11 pages.
Notice of Allowance mailed Nov. 19, 2015 for U.S. Appl. No. 13/769,036, filed Feb. 15, 2013, 9 pages.
Response filed Oct. 14, 2015 to Non Final Office Action mailed Jul. 16, 2015 for U.S. Appl. No. 13/769,036, filed Feb. 15, 2013, 17 pages.
Extended European Search Report for Application No. 13748661.9, mailed on Feb. 17, 2016, 12 pages.

* cited by examiner

ACTUATED CANNULA SEAL

RELATED APPLICATIONS

This application claims priority to U.S. Provisional Application Ser. No. 61/765,616 filed on Feb. 15, 2013, which is herein incorporated by reference in its entirety.

TECHNICAL FIELD

Embodiments of the present invention are related to seals, and in particular to cannula seals for minimally invasive robotic surgery.

DISCUSSION OF RELATED ART

Surgical procedures can be performed through a surgical robot in a minimally invasive manner. The benefits of a minimally invasive surgery are well known and include less patient trauma, less blood loss, and faster recovery times when compared to traditional, open incision surgery. In addition, the use of robot surgical systems (e.g., teleoperated robotic systems that provide telepresence), such as the da Vinci® Surgical System manufacture by Intuitive Surgical, Inc. of Sunnyvale, Calif., is known. Such teleoperated surgical systems may allow a surgeon to operate with intuitive control and increased precision when compared to manual minimally invasive surgeries.

In a minimally invasive surgical system, surgery is performed by a surgeon controlling the teleoperated robot. The robot includes one or more instruments that are coupled to arms. The instruments access the surgical area through small incisions through the skin of the patient. A cannula is inserted into the incision and a shaft of the instrument can be inserted through the cannula to access the surgical area. A seal between the cannula and the instrument shaft allows the incision to be sealed during the surgery. Existing cannula seals may have excessive, variable and direction dependent friction that can interfere with fine positioning and force sensing of the instrument tip in the insertion-retraction direction as it contacts surgical patient anatomy.

Therefore, there is a need to develop better performing cannula seals for minimum invasive surgical systems.

SUMMARY

In accordance with aspects of the present invention an actuated cannula seal and a system using the actuated cannula seal is presented. In some embodiments, a cannula seal includes a base portion that engages with a cannula; and a seal portion integrally formed with the base portion, the sealing portion capable of engaging with an instrument shaft, the sealing portion capable of being actuated by an actuator so that the sealing portion is continually in motion relative to the instrument shaft. The actuation of the sealing portion can be accomplished by rotation or vibration of the sealing portion relative to the instrument shaft.

A method of providing haptic feedback for motion along an instrument shaft according to some embodiments of the present invention can include actuating a cannula seal such that a sealing portion of the cannula seal is in motion with respect to the instrument shaft; measuring a force along the instrument shaft; correcting the measured force for modeled cannula seal friction; and transmitting the corrected force data to controls operated by a surgeon.

A system according to some embodiments of the present invention includes an actuated cannula seal that seals between a cannula and a surgical instrument; force sensors coupled to the surgical instrument, the force sensors sensing force along an axis of the surgical instrument; and a feedback system that receives force data from the force sensors and corrected the force data according to modeled cannula seal friction to form corrected force data.

These and other embodiments are further discussed below with respect to the following figures.

DETAILED DESCRIPTION

Figure 1A:
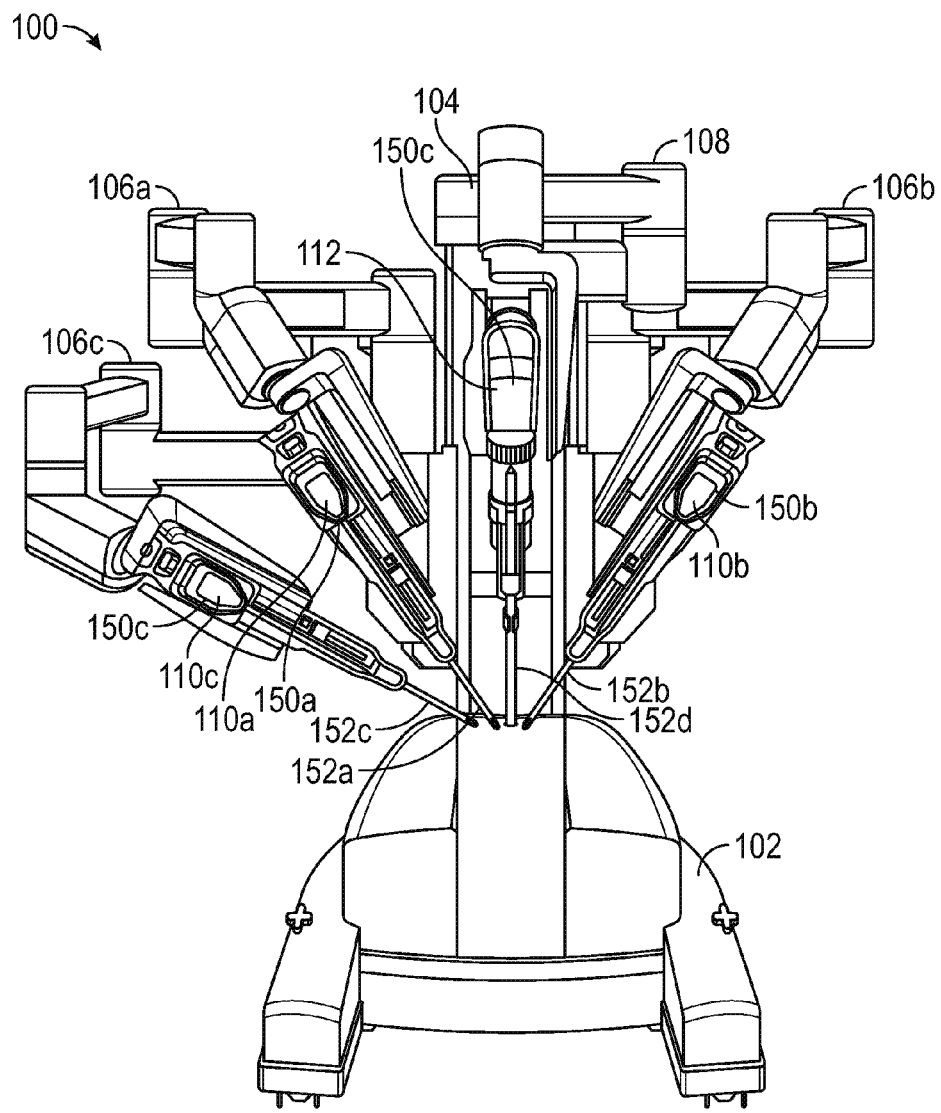
FIGS. 1A, 1B, and 1C illustrate components of an example teleoperated robotic surgical system.

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various mechanical, compositional, structural, and operational changes may be made without departing from the spirit and scope of this description and the claims. In some instances, well-known structures and techniques have not been shown or described in detail in order not to obscure the invention.

Additionally, the drawings are not to scale. Relative sizes of components are for illustrative purposes only and do not reflect the actual sizes that may occur in any actual embodiment of the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Aspects of embodiments of the invention are described within the context of a particular system. Knowledgeable persons will understand, however, that inventive aspects disclosed herein may be embodied and implemented in various ways, including robotic and non-robotic embodiments and implementations. Implementations described herein are merely exemplary and are not to be considered as limiting the scope of the inventive aspects disclosed herein. In particular, some embodiments of the invention assist in better force calculations along a surgical instrument in order to provide force information to the surgeon controlling the surgical robot.

Figure 1B:
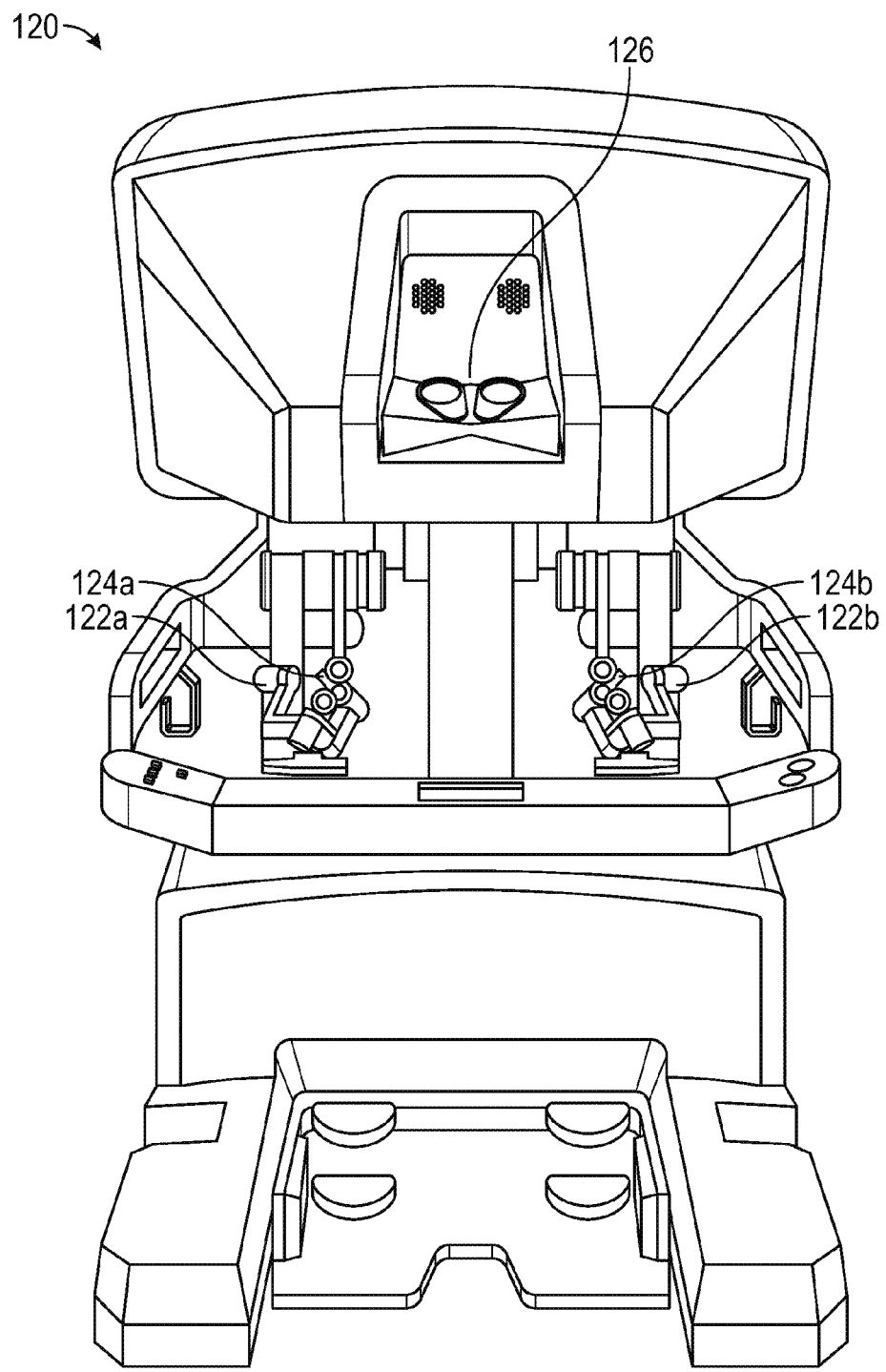
Figure 1C:
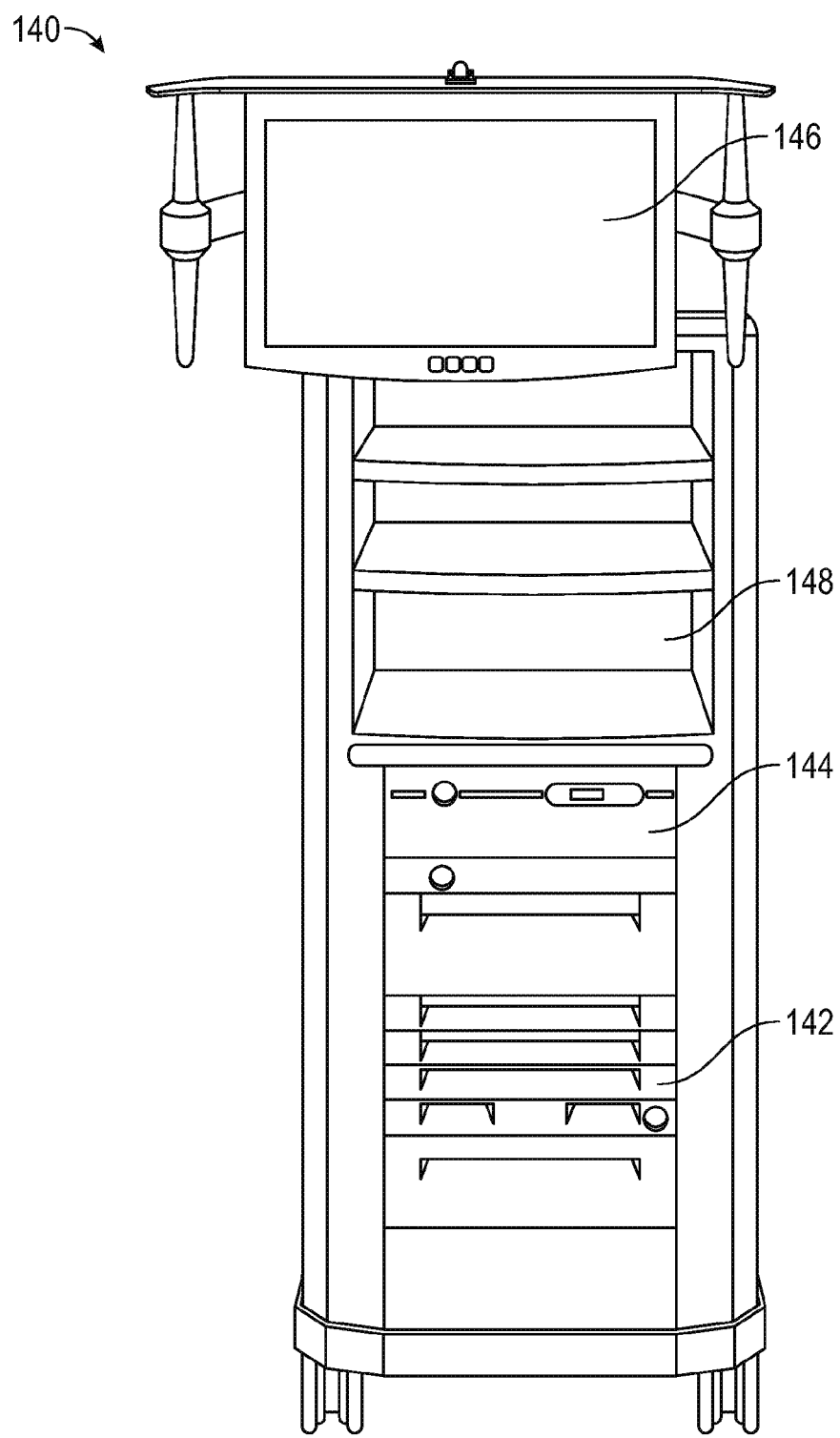

FIGS. 1A, 1B, and 1C are front elevation views of three main components of a teleoperated robotic surgical system for minimally invasive surgery. These three components are interconnected so as to allow a surgeon, with the assistance of a surgical team, to perform diagnostic and corrective surgical procedures on a patient.

FIG. 1A is a front elevation view of the patient side cart component 100 of a surgical system. The patient side cart includes a base 102 that rests on the floor, a support tower 104 that is mounted on the base 102, and several arms that support surgical tools. As shown in FIG. 1A, arms 106a, 106b, and 106c are instrument arms that support and move the surgical instruments used to manipulate tissue. Arm 108, for example, can be a camera arm that supports and moves an endoscope instrument 112. Instrument arm 106c can be an optional third instrument arm 106c that is supported on the back side of support tower 104 and that can be positioned to either the left or right side of the patient side cart as necessary to conduct a surgical procedure. FIG. 1A further shows interchangeable surgical instruments 110a,110b,110c mounted on the instrument arms 106a,106b,106c, and it shows endoscope 112 mounted on the camera arm 108. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

As is further illustrated in FIG. 1A, instruments 110a, 110b, 110c, and endoscope 112 include an instrument interface 150a, 150b, 150c, and 150d, respectively, and an instrument shaft 152a, 152b, 152c, and 152d, respectively. In some embodiments, component 100 can include supports for cannulas that fix instruments 110a, 110b, 110c, and endoscope 112 with respect to the cannulas.

Further, portions of each of the instrument arms 106a, 106b, and 106c are adjustable by personnel in the operating room in order to position instruments 110a, 110b, and 110c with respect to a patient. Other portions of arms 106a, 106b, and 106c are actuated and controlled by the surgeon at a surgeon's console 120. Surgical instruments 110a, 110b, 110c, and endoscope 112, can also be controlled by the surgeon at surgeon's console 120.

FIG. 1B is a front elevation view of a surgeon's console 120 component of a surgical system. The surgeon's console 120 is equipped with left and right multiple degrees of freedom (DOF) master tool manipulators (MTM's) 122a, 122b, which are kinematic chains that are used to control the surgical tools. The surgeon grasps a pincher assembly 124a, 124b on each MTM 122, typically with the thumb and forefinger, and can move the pincher assembly to various positions and orientations. When a tool control mode is selected, each MTM 122 is coupled to control a corresponding instrument arm 106 for the patient side cart 100. For example, left MTM 122a may be coupled to control instrument arm 106b and instrument 110a, and right MTM 122b may be coupled to control instrument arm 106b and instrument 110b. If the third instrument arm 106c is used during a surgical procedure and is positioned on the left side, then left MTM 122a can be switched between controlling arm 106a and instrument 110a to controlling arm 106c and instrument 110c. Likewise, if the third instrument arm 106c is used during a surgical procedure and is positioned on the right side, then right MTM 122a can be switched between controlling arm 106b and instrument 110b to controlling arm 106c and instrument 110c. In some instances, control assignments between MTM's 122a, 122b and arm 106a/instrument 110a combination and arm 106b/instrument 110b combination may also be exchanged. This may be done, for example, if the endoscope is rolled 180 degrees, so that the instrument moving in the endoscope's field of view appears to be on the same side as the MTM the surgeon is moving. The pincher assembly is typically used to operate a jawed surgical end effector (e.g., scissors, grasping retractor, needle driver, and the like) at the distal end of an instrument 110.

In accordance with certain aspects of the present invention, MTM's 122a, 122b can provide haptic force feedback to the surgeon. This force feedback allows the surgeon to more accurately control the MTM's so as to operate the jawed surgical end effectors of instruments 110a, 110b and 110c. Accurate sensing of forces on instruments 110a, 110b and 110c allows for a reliable force feedback, which allows the surgeon to more accurately control instruments 110a, 110b and 110c.

Surgeon's console 120 also includes a stereoscopic image display system 126. Left side and right side images captured by the stereoscopic endoscope 112 are output on corresponding left and right displays, which the surgeon perceives as a three-dimensional image on display system 126. In an advantageous configuration, the MTM's 122 are positioned below display system 126 so that the images of the surgical tools shown in the display appear to be co-located with the surgeon's hands below the display. This feature allows the surgeon to intuitively control the various surgical tools in the three-dimensional display as if watching the hands directly. Accordingly, the MTM servo control of the associated instrument arm and instrument is based on the endoscopic image reference frame. In accordance with certain aspects of the present invention, the stereoscopic image display 126 can also be used to visually display force feedback to the surgeon (e.g. a number corresponding to the magnitude of the applied force).

The endoscopic image reference frame is also used if the MTM's 122 are switched to a camera control mode. If the camera control mode is selected, the surgeon may move the distal end of the endoscope by moving one or both of the MTM's 122 together (portions of the two MTM's 122 may be servo-mechanically coupled so that the two MTM portions appear to move together as a unit). The surgeon may then intuitively move (e.g., pan, tilt, zoom) the displayed stereoscopic image by moving the MTM's 122 as if holding the image in the hands.

The surgeon's console 120 is typically located in the same operating room as the patient side cart 100, although it is positioned so that the surgeon operating the console is outside the sterile field. One or more assistants typically assist the surgeon by working within the sterile surgical field (e.g., to change tools on the patient side cart, to perform manual retraction, etc.). Accordingly, the surgeon operates remote from the sterile field, and so the console may be located in a separate room or building from the operating room. In some implementations, two consoles 120 (either co-located or remote from one another) may be networked together so that two surgeons can simultaneously view and control tools at the surgical site.

FIG. 1C is a front elevation view of a vision cart component 140 of a surgical system. The vision cart 140 houses the surgical system's central electronic data processing unit 142 and vision equipment 144. The central electronic data processing unit includes much of the data processing used to operate the surgical system. In various other implementations, however, the electronic data processing may be distributed in the surgeon console and patient side cart. The vision equipment includes camera control units for the left and right image capture functions of the stereoscopic endoscope 112. The vision equipment also includes illumination equipment (e.g., Xenon lamp) that provides illumination for imaging the surgical site. As shown in FIG. 1C, the vision cart includes an optional 24-inch touch screen monitor 146, which may be mounted elsewhere, such as on the patient side cart 100. The vision cart 140 further includes space 148 for optional auxiliary surgical equipment, such as electrosurgical units and insufflators. The patient side cart and the surgeon's console are coupled via optical fiber communications links to the vision cart so that the three components together act as a single teleoperated minimally invasive surgical system that provides an intuitive telepresence for the surgeon. And, as mentioned above, a second surgeon's console may be included so that a second surgeon can, e.g., proctor the first surgeon's work.

During a typical surgical procedure with the robotic surgical system described with reference to FIGS. 1A-1C, at least two incisions are made into the patient's body (usually with the use of a trocar to place the associated cannula). One incision is for the endoscope camera instrument, and the other incisions are for the surgical instruments. In some surgical procedures, several instrument and/or camera ports are utilized to provide access and imaging for a surgical site. Although the incisions are relatively small in comparison to larger incisions used for traditional open surgery, a minimum number of incisions is desired to further reduce patient trauma and for improved cosmesis.

Figure 2:
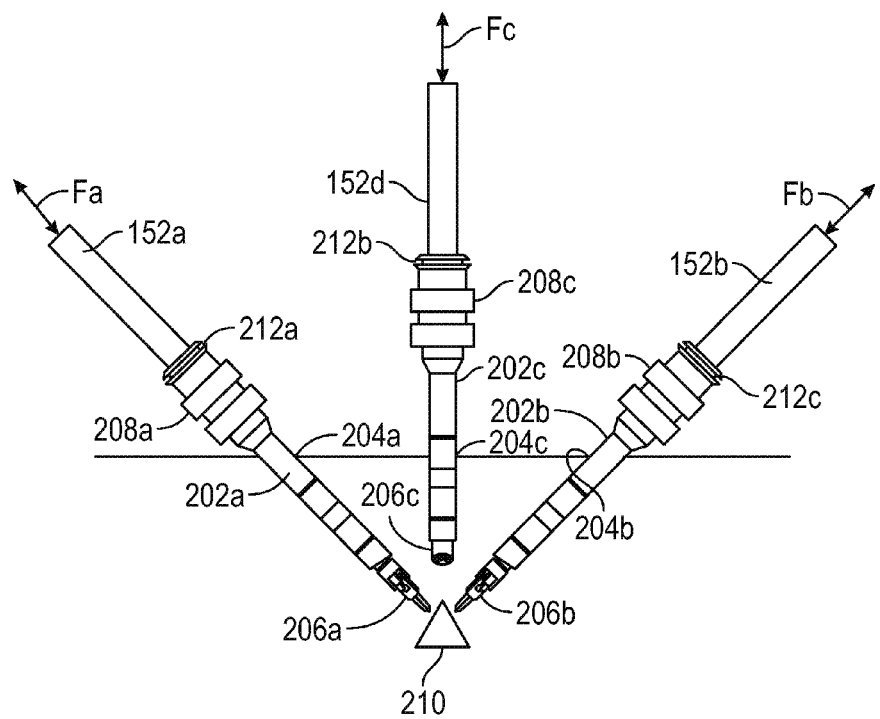
FIG. 2 illustrates cannulas as utilized by the system of FIGS. 1A, 1B, and 1C.

FIG. 2 illustrates utilization of the surgical instrument illustrated in FIGS. 1A, 1B, and 1C. As shown in FIG. 2, shafts 152a, 152b, and 152d pass through cannulas 202a, 202b, and 202c, respectively. Cannulas 202a, 202b, and 202c extend through instrument incisions 204a, 204b, and 204c, respectively. End effectors 206a, 206b, and 206c are attached to shafts 152a, 152b, and 152d, respectively. As discussed above, end effectors 206a, and 206b can be jawed surgical end effectors (e.g., scissors, grasping retractor, needle driver, and the like). Further, end effector 206c is illustrated as an endoscope tip. As shown in FIG. 2, cannulas 202a, 202b, and 202c and shafts 152a, 152b, and 152d are positioned so that end effectors 206a, 206b, and 206c operate in a surgical area 210.

As shown in FIG. 2 cannulas 202a, 202b, and 202c include mounting fittings 208a, 208b, and 208c, respectively, that can be engaged by arms 106a, 106b, and endoscope arm 108, respectively, to allow for very little movement of the instrument end effectors 206a, 206b, and 206c, respectively, as possible. Cannulas 202a, 202b, and 202c further include cannula seal mounts 212a, 212b, and 212c, respectively.

Cannula seals mounted to cannula seal mounts 212a, 212b, and 212c prevent leakage around shafts 152a, 152b, and 152d, respectively. During surgery, particularly if the surgery is abdominal surgery, pressurized $CO_2$ can be utilized to expand the abdomen, allowing for better access to surgical area 210. Further, cannula seals attached to cannula seal mounts 212a, 212b, and 212c prevent leakage of fluids or other materials from the patient.

During the operation, the surgeon sitting at surgeon's console 120 can manipulate end effectors 206a, 206b, and 206c as well as move shafts 152a, 152b, and 152d along force lines $F_a$, $F_b$, and $F_c$, respectively. These force lines represent forces along the insertion/retraction direction (i.e., the direction along shaft 152). Collectively, whether insertion or retraction, this direction may be referred to as the insertion direction.

Figure 3A:
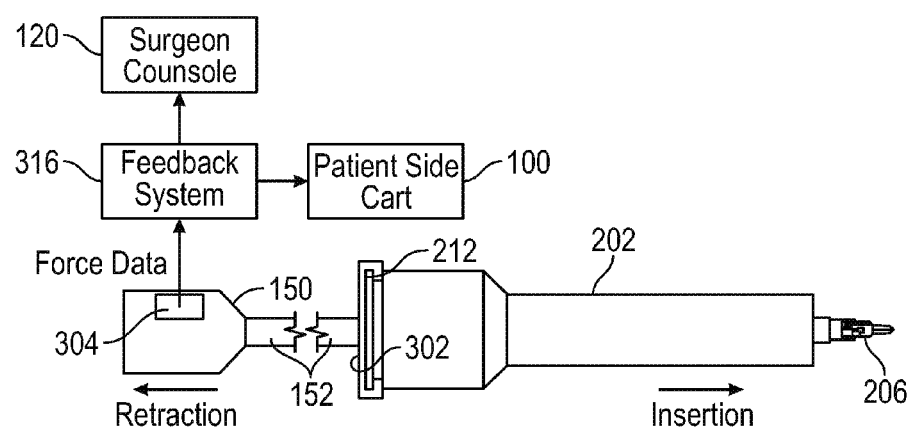
FIGS. 3A and 3B illustrate operation of a haptic feedback system according to some embodiments of the present invention.

As shown in FIG. 3A, utilizing various force measuring devices 304, the forces measured on end effectors 206a, 206b, and 206c can be used to provide force feedback to the surgeon at console 120, usually through resistance to the surgeon's input at MTMs 122, to allow the surgeon to control the force applied to end effectors 206a, 206b, and 206c and can also be used to counter frictional forces by compensating drivers in patient side cart 100.

FIG. 3A also illustrates a cannula seal 302 according to some embodiments of the present invention sealing shaft 152 and engaging cannula mount 212. As shown in FIG. 3A, force data is provided by measuring devices 304 to a haptic feedback system 316. Haptic feedback system 316 processes the force data and provides haptic feedback data to surgeon console 120. The haptic feedback data can be utilized to control motors and thus provide the resistance to the surgeon's input at MTMs 122. Additionally, or in place of controlling the motors directly, the haptic feedback data can be visually displayed to the surgeon on the surgeon's 3D visual display 126. Additionally, feedback data can be provided to patient side cart 100 to compensate instrument drivers.

Effective surgical instrument force feedback utilizes a full 3 dimensional sensing of the forces at end effectors 206 (collectively referring to end effectors 206a, 206b, and 206c). While satisfactory instrument shaft mounted force transducers provide good feedback for the transverse surgical forces applied to patient tissue through wrists and jaws of end effectors 206, wrist actuation cable forces utilized to operate end effectors 206 may prevent accurate sensing of surgical forces in the insertion direction (i.e., the direction along shafts 152 (collectively referring to shafts 152a, 152b, 152c, and 152d)) at the end effector. As a result, insertion direction forces are typically sensed at the back of surgical instruments 110 (collectively referring to surgical instruments 110a, 110b, 110c, and endoscope 112) at instrument interface 150 (collectively referring to instrument interfaces 150a, 150b, 150c, and 150d) or on arm 106 (collectively referring to arms 106a, 106b, and 106c or endoscope 112). In those cases, the frictional forces of shaft 152 sliding through cannula seals 302 mounted to cannula seal mount 212 (collectively referring to cannula seals mounts 212a, 212b, and 212c) becomes important, especially if that frictional force varies with direction (insertion or retraction), or velocity of shaft 152 through seal 212. In the discussion below, unequal insertion direction forces will be referred to as asymmetric while equal insertion and retraction forces will be referred to as symmetric. Cannula seal features in sliding contact with an inserted instrument shaft will also be referred to as symmetric when similar features face in opposite directions along the insertion direction or when such features do not point either way. Some embodiments of seal 302 according to the present invention substantially reduces or eliminates the static friction between seal 302 and instrument shaft 152, and therefore allow for more accurate feedback of forces to the operating surgeon. In some embodiments, cannula seal 302 is actuated such that seal 302 is in motion with respect to instrument shaft 152 at the contact between instrument shaft 152 and seal 302.

Figure 3B:
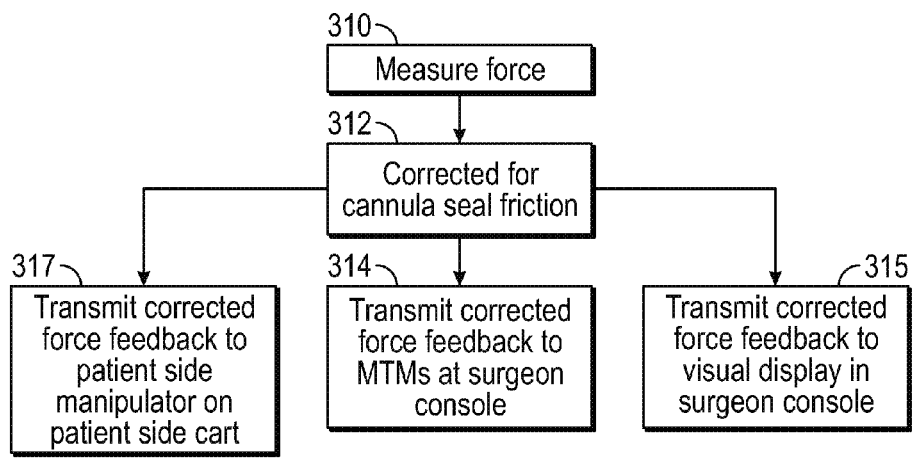

FIG. 3B illustrates an algorithm for processing the force data from force sensor 304. In some embodiments, the algorithm illustrated in FIG. 3B can be implemented in feedback system 316, which can be implemented by the surgeon's console 120. In some embodiments, the algorithm illustrated in FIG. 3B can be implemented in feedback system 316, which can be implemented by the patient side cart 100. In some embodiments, the algorithm illustrated in FIG. 3B can be implemented as visual feedback to the surgeon on the surgeon's visual display system 126. As shown in FIG. 3B, a force measurement is taken by force sensor 304 in step 310. In step 312, the force measurement is corrected for cannula seal friction. In step 312, the cannula seal friction using a cannula seal 302 according to some embodiments of the present invention can be predictable. In some embodiments, the cannula seal friction can be symmetric with respect to insertion and retraction direction. In some embodiments, the cannula seal friction can be substantially zero. In step 314, the corrected force can be used to provide haptic feedback to the surgeon at console 122, for example by applying a resistance force to the motion of a MTM 122. In step 315, the corrected force can be displaying to the surgeon on the 3D viewer. In step 317, the corrected force can be used in the patient side cart 100 as an input to the controller for the patient side manipulator to compensate for the measured resistive force.

Cannula seals have taken a number of forms including simple unidirectional compliant lip seals, tri-cuspid or multi-cuspid radial leaf seals, and spirally stacked overlapping and/or folded seal leaves akin to a traditional camera lens iris. Each of these types of seals have asymmetric construction which causes unequal seal frictional force depending on the direction of motion. Examples of seals that exhibit symmetrical force modeling are described in U.S. Pat. App. Ser. No. 61/599,288, which is herein incorporated by reference in its entirety.

Figure 4A:
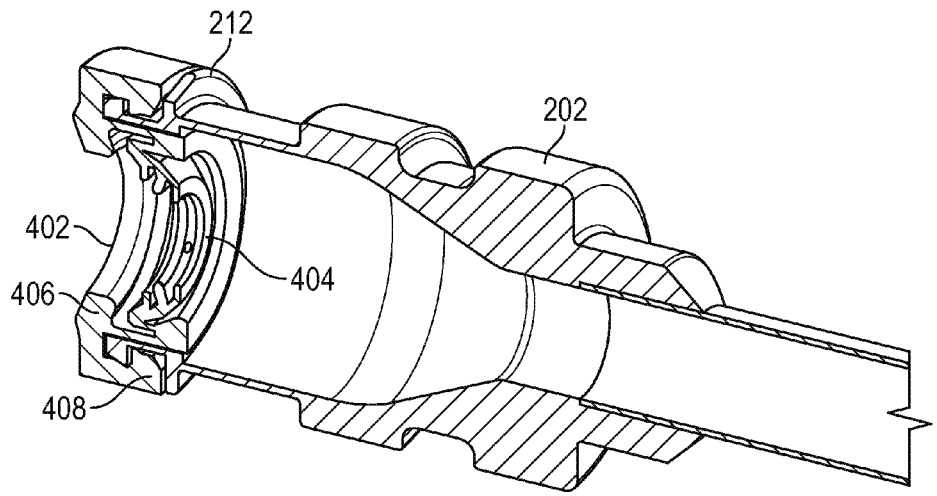
FIGS. 4A and 4B illustrate a cannula seal.
Figure 4B:
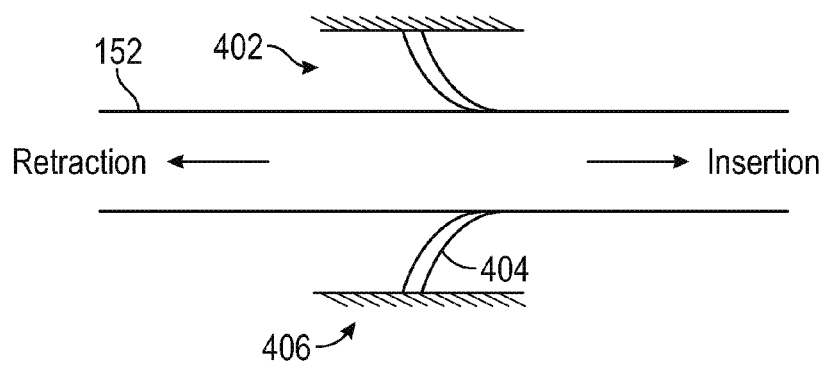

FIGS. 4A and 4B illustrate a conventional cannula seal 402. As shown in FIG. 4A, cannula seal 402 includes a base portion 406 and a retaining portion 408. Base portion 406 is attachable to cannula 202 at cannula seal mount 212 and is held in place by retaining portion 408, which is integrally formed with base portion 406. Retaining portion 408 also provides for sealing against cannula seal mount 212.

Further, cannula seal 402 includes a seal lip 404 that seals around shaft 152. FIG. 4B illustrates lip 404 sealing around shaft 152. As is illustrated in FIGS. 4A and 4B, lip 404 is asymmetric and is oriented in the insertion direction. Thus, shaft 152 will experience a different frictional force based on direction of motion. As is illustrated in FIG. 3B, lip 404 is oriented in a direction that facilitates motion of shaft 152 in the insertion direction. However, in the retraction direction, friction with shaft 152 compresses lip 304 about shaft 152 causing a much higher frictional force. In some cases, the ratio in force between insertion and retraction of shaft 152 can be a factor of about 1.5.

In some cases, especially with abdominal surgery, the direction of lip 404 assists in sealing against insufflation pressure. In abdominal surgery, pressurized $CO_2$ is provided into the abdomen by an insufflation system in order to expand the abdomen. $CO_2$ utilized in the insufflation system is typically supplied by a pressurized $CO_2$ tank and a regulator. The $CO_2$ pressure in the abdomen will load lip 304 by providing a force that pushes lip 404 more firmly against shaft 152.

Some other cannula seals have two transversely opposing lips like a shortened version of an oboe reed. Yet other seals have a simple compliant circular hole in a diaphragm. In this case, the deflection direction of the seal inverts, the result being that the seal lip faces in the direction opposite where it started, when motion of the shaft through the seal reverses direction, causing further uneven insertion friction force effects. Still other designs rely on an open compliant hole with a rigid plastic door that is pushed aside when the instrument shaft passes through the seal. In this case, the hinge direction of the door exerts asymmetric direction dependent friction forces on the instrument. In every case of existing seals, the forces are excessive, direction dependent, and vary too much with operating conditions to permit motion direction based subtraction of the expected friction forces from sensed forces to null out the frictional effects. The expected friction force contribution may be based on experimental measurements. Therefore, utilizing these seals, the frictional force provides for unreliable force feedback to the surgeon.

Other than the application of lubricant, this problem has not been addressed. Some manufacturers of laparoscopic cannula seals provide a separately packaged pouch of lubricant such as silicone or purified (white mineral oil based) petroleum grease for optional use or pre-coat the seal with such a grease. Silicone or other rubber materials utilized as a seal have a relatively high dry coefficient of friction. Grease lubricants help but do not sufficiently reduce seal friction and may wipe off during a procedure so that the friction varies with time. Grease lubricants also do not equalize the direction dependent forces due to asymmetric seal lip design. Therefore, addition of lubricating materials alone does not significantly help with the asymmetric frictional forces applied when the instrument shaft is moved through a seal.

In some embodiments, the noise limited force sensitivity of a transverse instrument force transducer allows measurement of forces significantly lower than the frictional forces on existing cannula seals. Therefore, the combined effect of all parasitic insertion forces on instrument 110 between a shaft face 152 and cannula seal 302 may be greater than the transverse force transducer sensitivity. It may be possible to improve the transverse force sensitivity further in the future, resulting in a need for a similar improvement in the force sensitivity in the axial direction. Greased seals in combination with present seal designs cannot accomplish the sensitivity needed to provide for reliable force feedback to the surgeon.

Experimental coating of existing molded silicone rubber seals with a dry lubricant parylene managed to reduce the friction between the shaft and the seal by a factor of approximately 4 as opposed to the uncoated seal. The force can be measured with a handheld force gauge. However, the asymmetric nature of the friction caused by conventional seal lips causes a difference in the friction depending on the direction of motion of the shaft through the seal. This asymmetric nature detrimentally affects the ability of the force applied at the effector to be determined by the surgeon.

In particular, in order to provide for a highly reliable indication of the force along shaft 152, both in insertion and retraction, it is desirable that the frictional force between cannula seal 302 attached to cannula seal mount 212 be as symmetric as possible with respect to direction of motion and as uniform as possible during motion. In that case, an estimate of the frictional force can be subtracted from the insertion direction forces measured by a sensor. It is also desirable that the frictional force be as low as possible in order to minimize any remaining error in the improved estimate of the insertion direction surgical force on patient tissue obtained by subtracting the estimated friction force from the sensor measured force.

Friction between instrument shaft 152 and cannula seal 302 are a major source of force noise for force sensors 304 trying to sense force applied at end effector 206 from outside the body. This is especially true for force sensors 304 that sense forces along the insertion axis of instrument shaft 152.

Figure 5A:
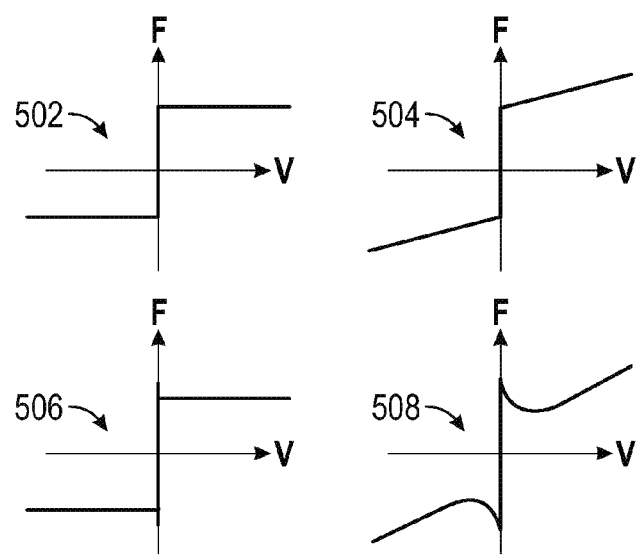
FIGS. 5A and 5B illustrate force models that can be utilized in some embodiments of the present invention.
Figure 5B:
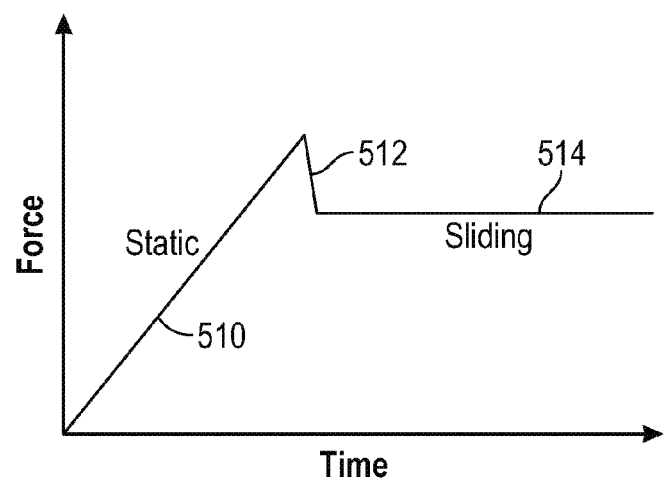

The friction between instrument shaft 152 and cannula seal 302 can be modeled with a variety of models. FIG. 5A shows graphs illustrating four of those models. Graph 502 shows force versus velocity in a model of Coulomb friction. Graph 504 shows force versus velocity in a model that combines Coulomb and viscous factors. Graph 506 shows force versus velocity in a model that combines Static friction, Coulomb friction, and viscous friction. Graph 508 shows force versus velocity in a Stribeck model. FIG. 5B illustrates the force versus time in a model that combines Static friction, Coulomb friction, and viscous friction. As shown in FIG. 5B, the force increases during a static period 510 until movement is started at point 512, after which a constant force can provide for sliding in period 514. Static period 510 can vary and can be difficult to precisely model.

The modeled force can be subtracted from the force readings from force sensor 304 in step 312. However, the problem with modeling the static period 510 is that the friction force can vary greatly with no resulting movement of the system. Therefore, it is difficult to correctly predict which point along the curve illustrated in FIG. 5B is correct for a given force and position. Additionally, friction models can vary as parts wear and if fluids are applied between the surfaces (e.g. blood, saline, or other fluids) or the fluids vary over time.

Embodiments of the present invention include a dynamically actuated cannula seal 302 such that the model utilized can be in the sliding period 514 shown in FIG. 5B. The interaction friction between cannula seal 302 and instrument shaft 152 is therefore that of kinetic (dynamic) friction, which eliminates any static friction (or stiction) between seal 302 and instrument shaft 152. In almost all materials, the coefficient of kinetic friction is lower than that of static friction. Therefore, the frictional force from such a dynamic interaction is lower than static friction force at point 512 (just before movement). Additionally, the dynamic force as shown in period 514 of FIG. 5B is more uniform, accurate, and predictable. Therefore, the model used for determining the friction between seal 302 and instrument shaft 152 so that it can be subtracted from the measured force in step 312 is more uniform, accurate, and predictable as well.

Figure 6A:
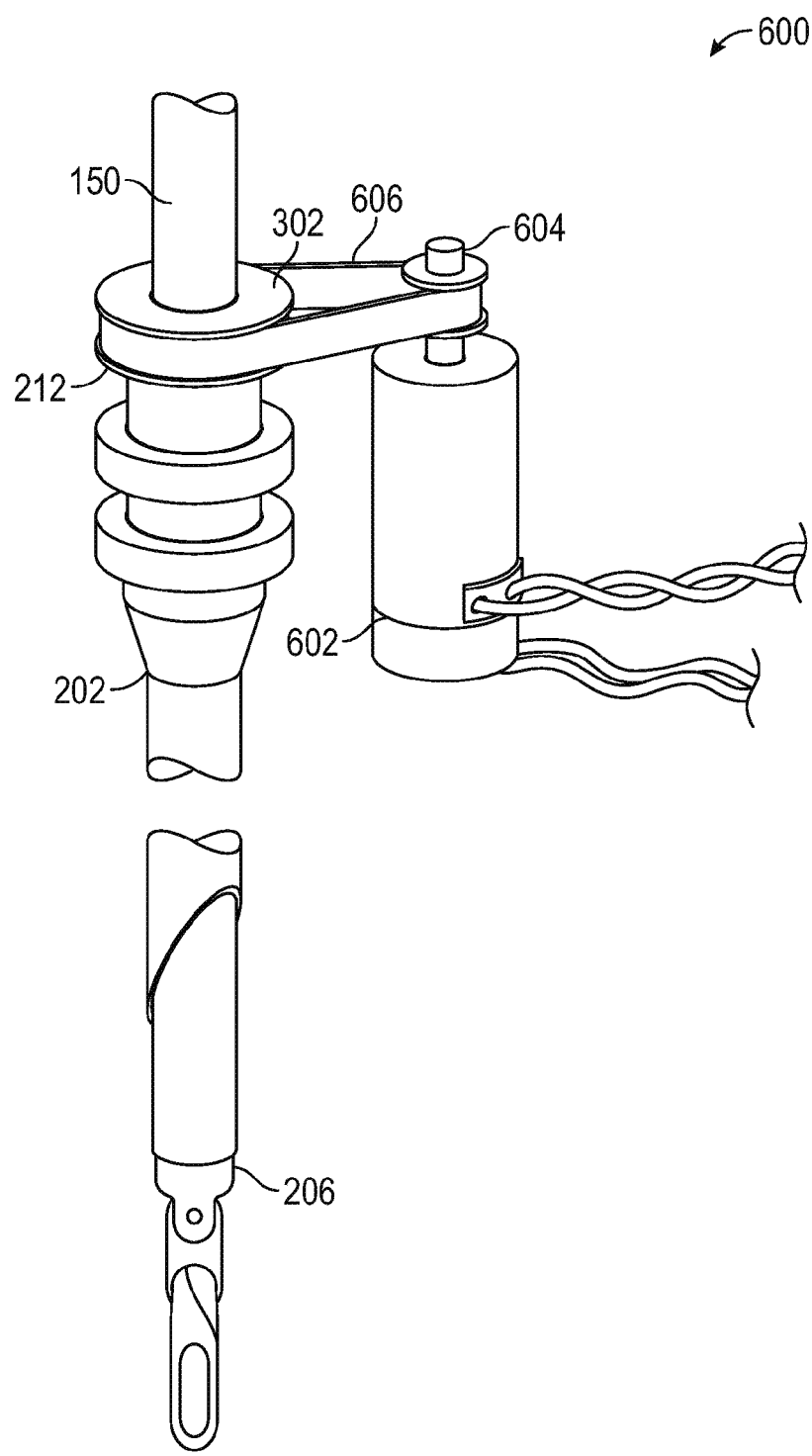
FIGS. 6A, 6B, and 6C illustrate an actuated cannula seal according to some embodiments of the present invention.
Figure 6B:
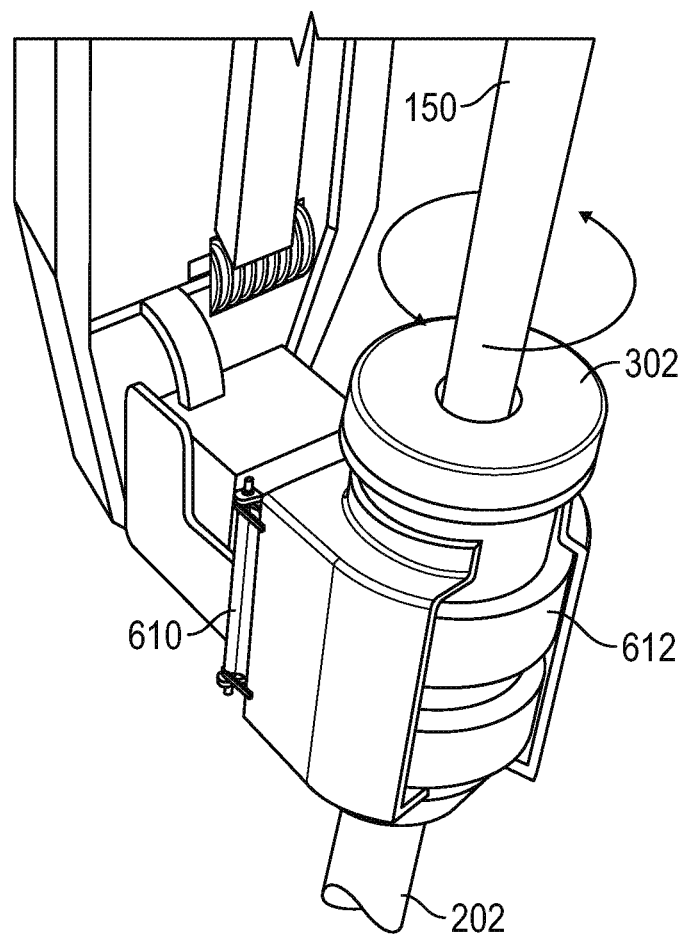

FIGS. 6A and 6B illustrate an embodiment of a seal 302 and actuator 600 that continuously rotates seal 302 on instrument shaft 152. As shown in FIG. 6A, actuator 600 includes a motor 602 that drives a pulley 604. A drive belt 606 couples pulley 604 with shaft seal 302. In some cases, actuator 600 may rotate shaft seal 302 without rotating any part of cannula 202. In some embodiments, shaft seal 302 may be mounted on a cannula part that rotates with shaft seal 302.

Figure 6C:
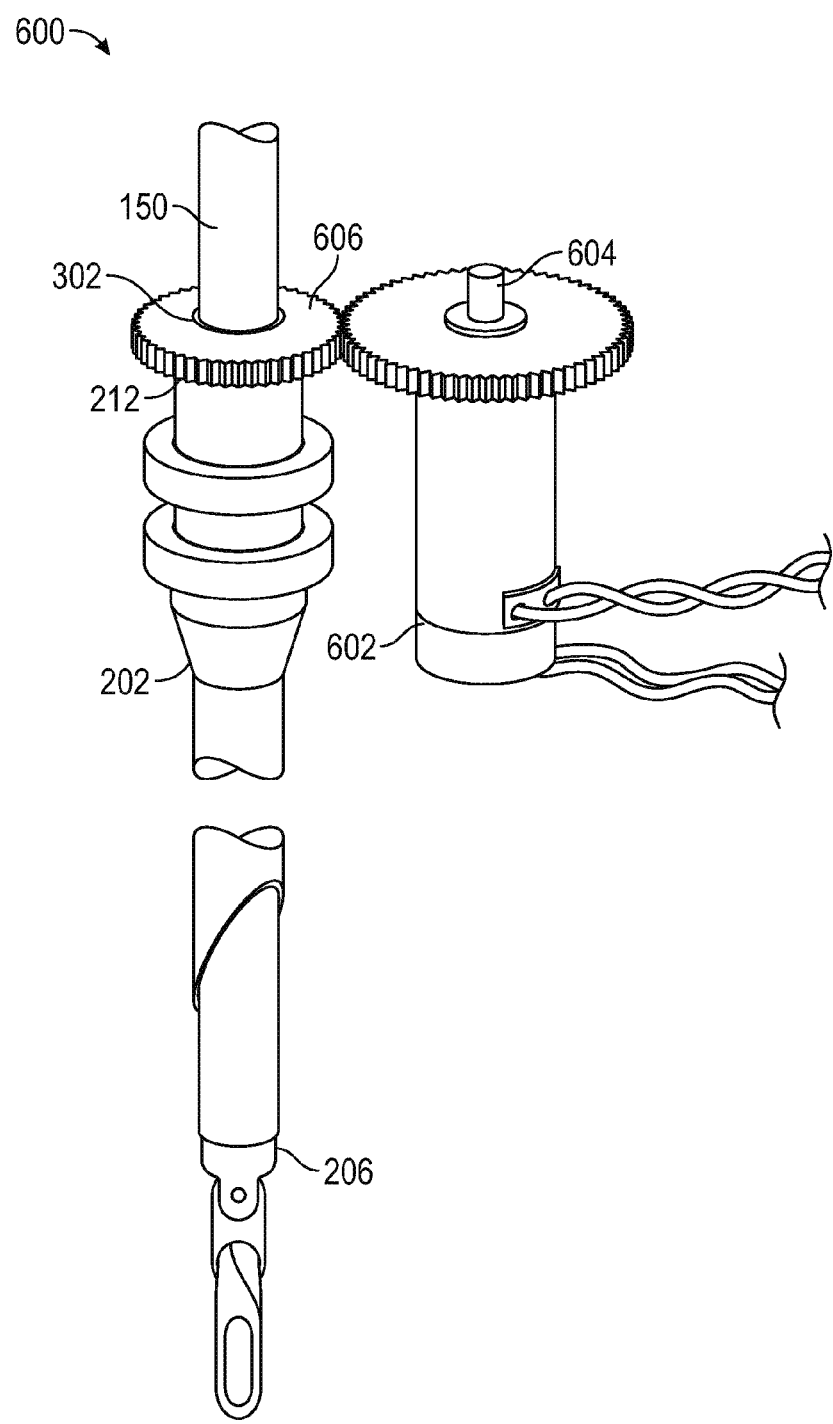

In some embodiments, motor 602 of actuator 600 can be an electric motor or a pneumatic motor or a piezo motor. In FIG. 6A, motor 602 is shown with a drive pulley 604 and drive belt 606. In some embodiments, motor 602 may be mechanically coupled to rotate seal 302 with a gear drive or other drive mechanism. In some embodiments, for example, actuator 600 can include a gear that engages a gear connected to seal 302, as shown in FIG. 6C, or a gear connected to a rotatable portion of cannula 202 to rotate seal 302.

If motor 602 is a pneumatic motor, motor 602 can utilize the pressure difference between the insufflated inner lumen and the patient's exterior to drive pulley 604. A pneumatically driven motor can also be driven by an external pressure source.

FIG. 6B illustrates further parts of actuator 600 and seal 302. As shown in FIG. 6B, seal 302 is rotated around shaft 150. Cannula 202 is held in jaws 610 that engage cannula 202 at adaptor 612. Seal 302 is attached to adaptor 612. In some embodiments, adaptor 612 is rotatable on cannula 202 and jaws 610 can include a motor that directly drives adaptor 612, which rotates seal 302.

Figure 7A:
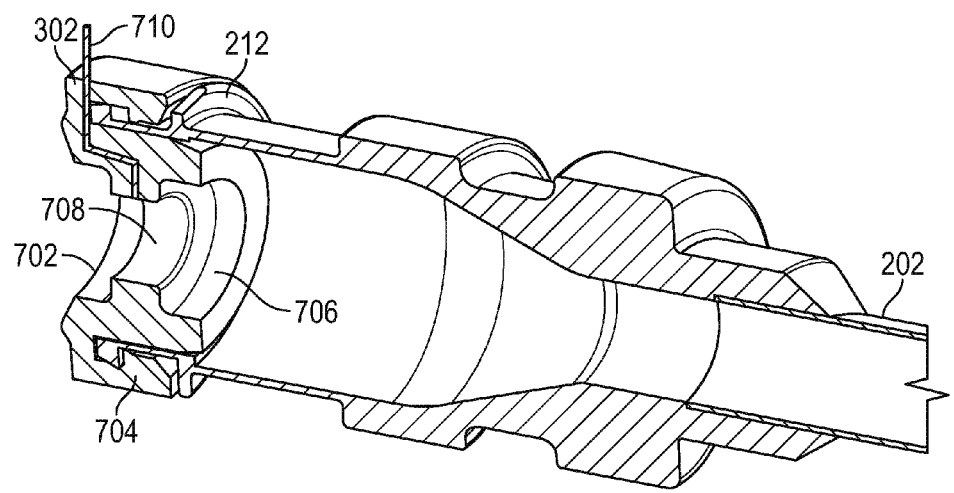
FIG. 7A illustrates an actuated cannula seal with a piezoelectric actuator according to some embodiments of the present invention.

FIG. 7A illustrates another embodiment of seal 302. As shown in FIG. 7A, seal 302 is attached to seal mount 212. Seal 302 includes a body 702, an integrally formed retaining portion 704, and an integrally formed seal portion 706. As shown in FIG. 7A, retaining portion 704 engages with seal mount 212 of cannula 202 to hold seal body 702 in place. Seal portion 706 extends from seal body 702 to surround an instrument shaft that is inserted through cannula 202. As is further shown in FIG. 7A, seal portion 706 is coupled to a piezoelectric actuator 708. Actuator 708 can vibrate or oscillate the material of seal 706 or an instrument shaft. Actuator 708 can, for example, be a piezopolymer, that vibrates seal portion 706 to reduce or substantially eliminate static friction between cannula seal 302 and instrument shaft 152. For example, as shown in FIG. 7A, actuator 708 of seal portion 706 can be formed of a piezopolymer such as Polyvinylidene fluoride (PVDF), for example. Actuator 708 can be formed anywhere within seal portion 706 so a sealing material that contacts an inserted surgical instrument shaft 152 can be actuated. In either case, the piezopolymer vibrates seal portion 706 to prevent static contact with instrument shaft 152, eliminating static friction. As shown in FIG. 7, wiring 710 can be embedded within body 702 of seal 302 and used to electrically drive actuator 708.

Figure 7B:
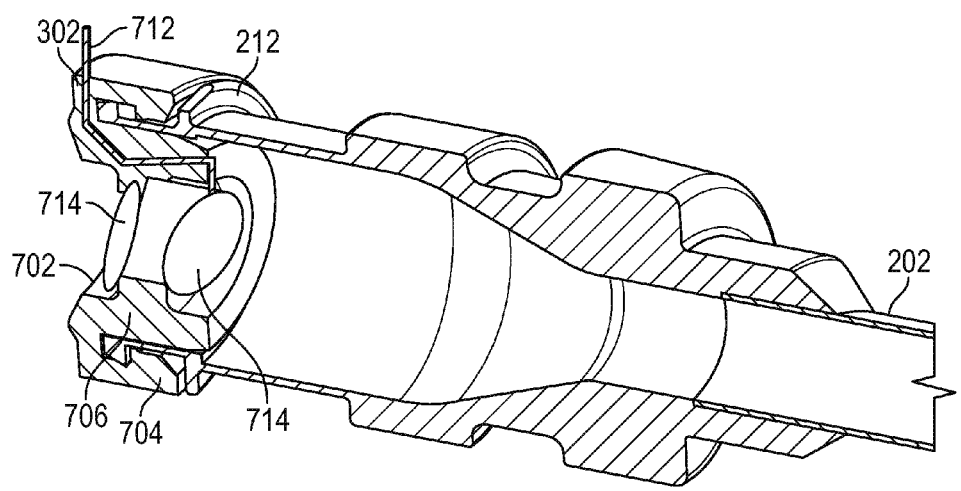
FIG. 7B illustrates an actuated cannula seal with a voice coil actuator according to some embodiments of the present invention.

FIG. 7B illustrates an embodiment of actuated seal 302 that is driven by a voice coil actuator 714 that can vibrate sealing portion 706 (for example axially) and maintain transient slipping contact with the instrument shaft. As shown in FIG. 7B, electrical connections 712 to voice coil actuator 714 can be embedded within body 702 of seal 302. Alternatively, voice coil actuator 714 can be independent of seal 302 and inserted into cannula 202 prior to seal 302 such that seal 302 contacts voice coil actuator 714. In which case, electrical connections 712 can be directed through the side of cannula 202. In some embodiments, voice coil actuator 714 can include two voice coils positioned on either side of sealing portion 706. In some embodiments, the two voice coils can be driven oppositely to one another such that sealing portion 706 is symmetrically under expansion or contraction.

Figure 8A:
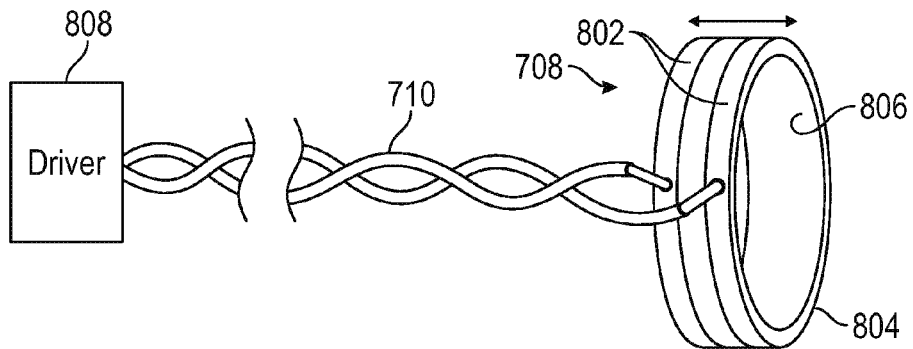
FIGS. 8A, 8B, and 8C illustrate some example embodiments of piezoelectric actuators that can be used in the actuated cannula seal illustrated in FIG. 7A.
Figure 8B:
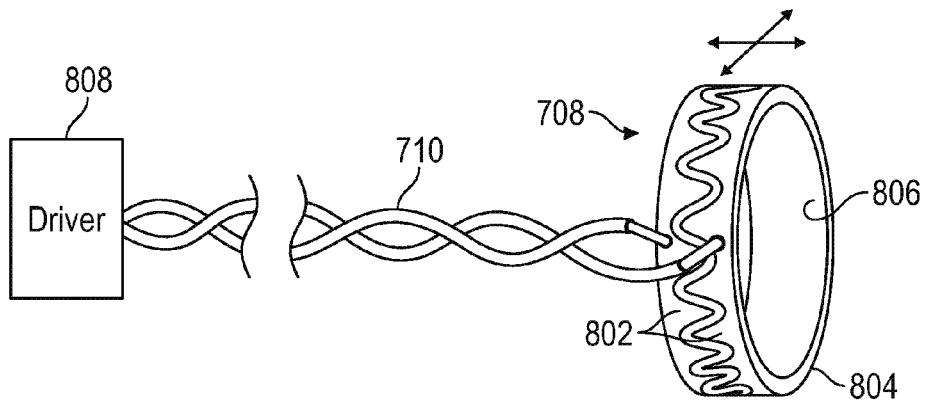
Figure 8C:
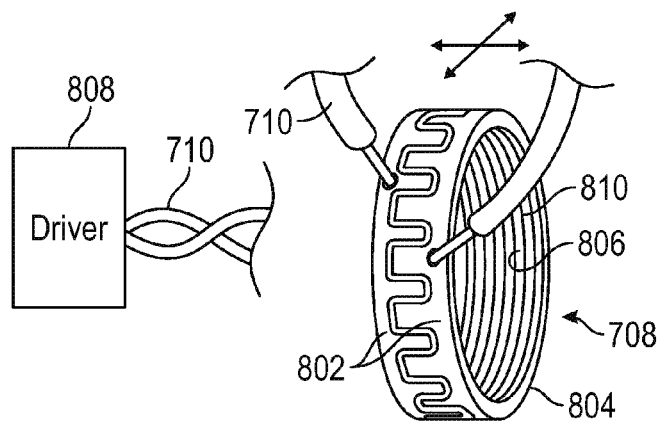

FIGS. 8A, 8B, and 8C illustrate some example embodiments of actuator 708 as illustrated in FIG. 7. In the embodiment illustrated in FIG. 8A, actuator 708 includes a ring-shaped piezoelectric material 804. As discussed above, piezoelectric material can be a piezopolymer such as PVDF. As shown in FIG. 8A, electrodes 802 are arranged around the outside diameter of piezoelectric material 804. The inside diameter of piezoelectric material 804 can be lined with a sealing material 806. Sealing material 806 can be a lower friction material. Actuator 708 is sized so that the shaft of a surgical instrument is in close sliding or actual contact with sealing material 806. Electrodes 802 can be coupled to a driver 808 with wires 710. Wires 710 can be embedded in body 702 and extend from seal 302, as is illustrated in FIG. 7. Wires 710 are coupled to a driver 808, which electrically drives electrodes 802. Driver 808 can produce an oscillating voltage, for example a square wave voltage. The driving voltage can be of a strength and frequency to provide for continuous motion of material 806 against instrument shaft 152 with high enough frequency that the vibration is undetectable to the surgeon (e.g., above about 1 kHz) or does not interfere with the surgeon's sense of touch.

Electrodes 802 in the example illustrated in FIG. 8A are separated solid rings. As a result, voltage applied to electrodes 802 result in axial expansion and contraction (i.e. along the long axis of an instrument shaft inserted through actuator 708) of actuator 802. The driving voltage from driver 808 can be of a strength and frequency to provide for continuous motion of material 806 against instrument shaft 152.

Further, in some embodiments the driving frequency can be high enough to prevent interference with other sensors in the surgical environment. In some embodiments, the force data from sensor 304 can be filtered to remove signals at the driving frequency to remove any influence of the actuation from the force data. In either case, the vibrations caused by driving the piezoelectric material do not result in haptic feedback to the operator in step 314 of FIG. 3B or feedback to the patient side manipulator in 317.

Electrodes 802 in the example illustrated in FIG. 8B are partially interdigitated. This may reduce the axial motion of actuator 708, but introduces an expansion and contraction motion. In this embodiment, the grip between material 806 and an instrument shaft 152 and the axial location of material 806 with respect to instrument shaft is periodic. The result is that material 806 is in constant motion with respect to instrument shaft 152.

Electrodes 802 in the example of actuator 708 illustrated in FIG. 8C are interdigitated more fully than the example illustrated in FIG. 8B. As a result, the axial motion of actuator 708 can be greatly reduced and the expansion and contraction of actuator 708 can be the primary motion. This results in a periodicity in the contact between material 806 and instrument shaft 152. In some embodiments, contact between instrument shaft 152 and material 806 can be periodically broken. This motion will prevent material 806 from exhibiting static friction against instrument shaft 152. The additional axial motion can further prevent any remaining static friction between material 806 and instrument shaft 152.

FIG. 8C also illustrates that material 806 can include ridges 810. Material 806 in the examples illustrated in FIGS. 8A and 8B may also include ridges 810. Ridges 810 can provide a seal against instrument shaft 152 while reducing the contact area between material 810 and instrument shaft 152.

Figure 9A:
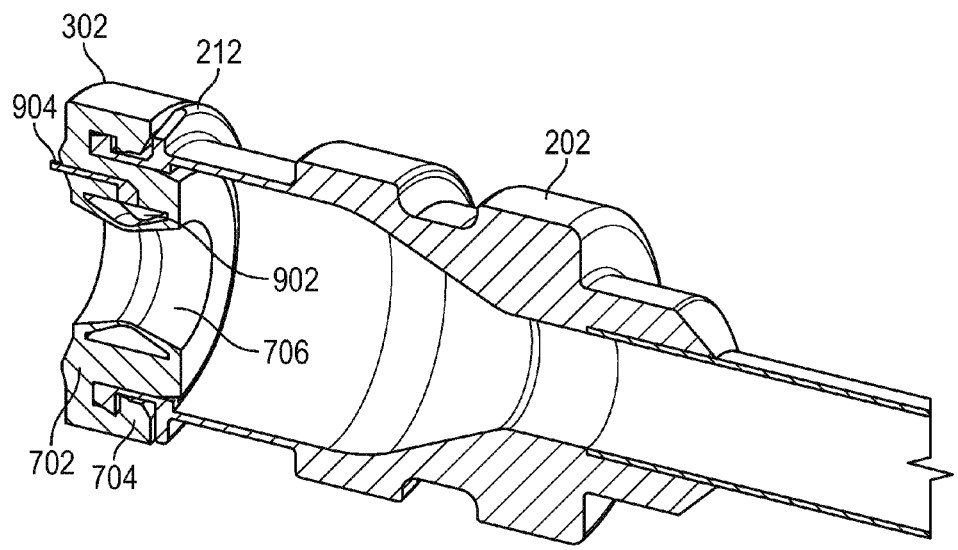
FIGS. 9A and 9B illustrate an actuated seal with a pneumatic actuator according to some embodiments of the present invention.
Figure 9B:
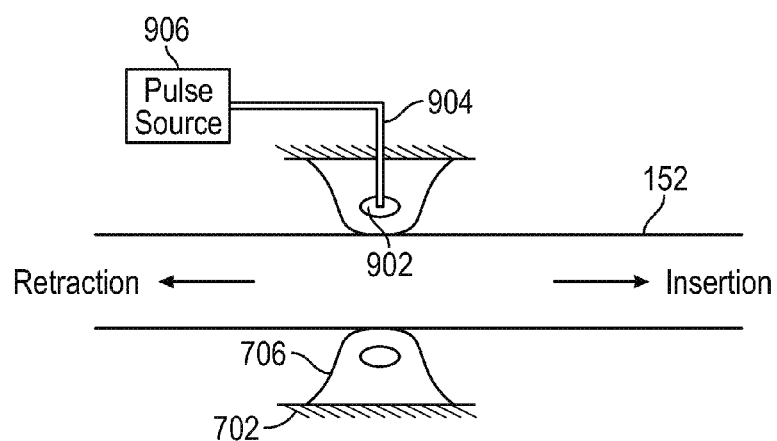

FIGS. 9A and 9B illustrate an embodiment of seal 302 that utilizes a pressure driven actuator. In the embodiment of seal 302 illustrated in FIG. 9A, sealing portion 706 includes a cavity 902. The pressure within cavity 902 can be modulated through passageway 904. FIG. 9B illustrates the interaction between sealing portion 706 and instrument shaft 152. As shown in FIG. 9B, sealing portion 706 engages instrument shaft 152 when cavity 902 is pressurized. In some embodiments, cavity 902 may not engage instrument shaft 152 when it is unpressurized. Pulse source 906 can provide pressure pulses through passageway 904 to cavity 902 such that sealing portion 706 periodically engages instrument shaft 152. Consequently, the material of sealing portion 706 is in motion relative to instrument shaft 152 reducing the static friction between sealing portion 706 and instrument shaft 152.

The pressure pulses can be of low frequency or high frequency. As discussed above, high frequency pulses can be filtered from the force data generated by sensor 304 so that a surgeon operating the instrument does not feel that vibration. In some cases, the frequency can be as high as, for example, 1 kHz, and may be generated as an audible tone transmitted through passageway 904. Furthermore, the amplitude of the pulse, which correlates with the size of the vibration imparted to sealing portion 706 from chamber 902, may not be large. It is sufficient that sealing portion 706 be actuated where sealing portion 706 contacts instrument shaft 152 so that sealing portion 706 is in motion resulting in a reduction of the static friction between sealing portion 706 and instrument shaft 152.

As discussed above, embodiments of seal 302 can be actuated in a constant, oscillatory, or intermittent motion. The actuation motion may result in rotary, axial, or diametric motions. Axial motion may be divided between opposite motions of two annular portions of sealing portion 706 of seal 302 that contact the surface instrument shaft 152 so that there is no net axial force applied to instrument shaft 152. In some embodiments, sealing portion 706 of seal 302 is rotated or vibrated only as the instrument shaft's velocity along the insertion axis of the instrument is below a threshold value close to zero (0). If the motion of seal 302 is not constant relative to the instrument shaft, the driving frequency of seal 302 may be high enough to not affect the control system of the manipulator that controls any instrument in the surgical area and further may be high enough to be above the sensed frequency of any sensors within the surgical area. In some cases, filtering may be used to remove noise artifacts in force sensor 304 or other sensors in the area that may be due to a vibratory excitation of cannula seal 302.

The above detailed description is provided to illustrate specific embodiments of the present invention and is not intended to be limiting. Numerous variations and modifications within the scope of the present invention are possible. The present invention is set forth in the following claims.

What is claimed is:

1. A surgical system, comprising:
a controller;
an arm coupled to the controller;
a surgical instrument coupled to the arm and controlled by the controller, the surgical instrument including an instrument shaft;
cannula, the instrument shaft being received through the cannula;
a cannula seal coupled to the cannula, the cannula seal including a base portion that engages with the cannula and a seal portion coupled to the base portion, the seal portion being sized and shaped to slidably engage the instrument shaft; and
an actuator coupled to the cannula seal, the actuator being configured to induce continuous rotation of the seal portion relative to the instrument shaft.

2. The surgical system of claim 1, wherein the actuator includes a motor that rotates the seal portion relative to the instrument shaft.

3. The surgical system of claim 2, wherein the motor is an electric motor.

4. The surgical system of claim 2, wherein the motor is a pneumatic motor.

5. The surgical system of claim 4, wherein the pneumatic motor is driven by insufflation pressure.

6. The surgical system of claim 2, wherein the motor is coupled to the base portion of the cannula seal with a drive belt, and wherein rotation of the base portion induces rotation of the seal portion relative to the instrument shaft.

7. The surgical system of claim 2, wherein the motor is coupled to the base portion of the cannula seal through a gear, and wherein rotation of the base portion induces rotation of the seal portion relative to the instrument shaft.

8. The surgical system of claim 1, wherein the actuator includes a piezoelectric actuator.

9. The surgical system of claim 8, wherein the piezoelectric actuator is formed from a piezopolymer.

10. The surgical system of claim 8, wherein the piezoelectric actuator is formed in a ring integrated with the seal portion.

11. The surgical system of claim 10, wherein the piezoelectric actuator includes electrodes arranged around an outside diameter of the ring.

12. The surgical system of claim 11, wherein the electrodes include separated rings arranged around the outside diameter of the ring.

13. The surgical system of claim 11, wherein the electrodes are separated and partially interdigitated electrodes.

14. The surgical system of claim 11, wherein the electrodes are interdigitated electrodes.

15. The surgical system of claim 11, wherein the electrodes are driven at a frequency high enough not to interfere with a surgeon's sense of touch.

16. The surgical system of claim 1, wherein the actuator includes at least one voice coil in contact with the seal portion.

17. The surgical system of claim 16, wherein the actuator includes two voice coils on either side of the seal portion, the two voice coils being driven oppositely to one another.

18. The surgical system of claim 16, wherein the at least one voice coil is driven at a frequency high enough to not interfere with a surgeon's sense of touch.

19. The surgical system of claim 1, wherein the actuator is configured to pneumatically pulse a cavity defined at least in part by the seal portion.

20. The surgical system of claim 19, wherein the actuator pneumatically pulses at a pulse frequency that is high enough to not interfere with a surgeon's sense of touch.

21. A method of providing haptic feedback comprising:
actuating a cannula seal such that a sealing portion of the cannula seal is in continuous rotary motion with respect to an instrument shaft;
measuring a force along the instrument shaft;
correcting the measured force for modeled cannula seal friction to produce corrected force data; and
transmitting the corrected force data to controls that are operable by a surgeon.

22. The method of claim 21, wherein correcting the measured force includes filtering the measured force to reject a frequency of the actuation.

23. The method of claim 21, wherein actuating the cannula seal includes continuously rotating the cannula seal relative to the instrument shaft using a drive belt that is coupled to the cannula seal.

24. The method of claim 21, wherein actuating the cannula seal includes driving a piezoelectric actuator coupled to the sealing portion of the cannula seal.

25. The method of claim 21, wherein actuating the cannula seal includes driving one or more voice coils in contact with the sealing portion of the cannula seal.

26. The method of claim 21, wherein actuating the cannula seal includes pneumatically vibrating a cavity in the sealing portion of the cannula seal.

27. The method of claim 21, wherein transmitting the corrected force data to controls includes providing haptic feedback through the controls.

28. The method of claim 21, wherein transmitting the corrected force data to controls includes displaying the corrected force data on a display.

29. The method of claim 21, further including correcting force inputs based on the corrected force data.

30. A system, comprising:
an actuated cannula seal including a seal portion that seals between a cannula and a surgical instrument, and an actuator configured to induce continuous rotation of the seal portion relative to the surgical instrument;
force sensors coupled to the surgical instrument, the force sensors sensing force along an axis of the surgical instrument; and
a feedback system that receives force data from the force sensors and corrects the force data according to modeled cannula seal friction to form corrected force data.

31. The system according to claim 30, wherein the actuated cannula seal is actuated by rotation of the seal portion around the axis of the surgical instrument using a drive belt coupled to the seal portion.

32. The system of claim 30, wherein the actuated cannula seal is actuated by a piezoelectric actuator integrated with the actuated cannula seal.

33. The system of claim 30, wherein the actuated cannula seal is actuated with pneumatic pulses.

34. The system of claim 30, wherein the feedback system filters a frequency of actuation of the actuated cannula seal.

35. The system of claim 30, wherein a frequency of actuation of the actuated cannula seal is high enough to not interfere with a surgeon's touch.

36. The system of claim 30, wherein the corrected force data is transmitted to a surgeon's console to provide haptic feedback.

37. The system of claim 30, wherein the corrected force data is displayed on a surgeon's console.

38. The system of claim 30, wherein the corrected force data is used to provide force compensation at a patient side cart.

39. A surgical system, comprising:
a controller;
an arm coupled to the controller;
a surgical instrument coupled to the arm and controlled by the controller, the surgical instrument including an instrument shaft and a force sensor;
cannula receiving the instrument shaft of the surgical instrument; and
an actuated cannula seal attached to the cannula and engaging the instrument shaft of the surgical instrument, the actuated cannula seal including a base portion that engages with the cannula and a sealing portion integrally formed with the base portion that slidably engages with the instrument shaft, at least the sealing portion of the actuated cannula seal being actuated such that the sealing portion is in motion relative to the instrument shaft;
wherein the controller executes code that receives force measurements from the force sensor, corrects the force measurements for friction between the cannula seal and the instrument shaft to generate corrected force feedback, and transmits the corrected force feedback to a master tool manipulator on the controller.

40. The surgical system of claim 39, wherein the sealing portion of the actuated cannula seal is in constant, oscillatory, or intermittent motion relative to the instrument shaft.

41. The surgical system of claim 39, wherein the motion of the sealing portion relative to the instrument shaft substantially reduces or eliminates static friction between the sealing portion and the instrument shaft.

42. The surgical system of claim 39, wherein:
the instrument shaft includes a proximal end, a distal end, and an axis extending from the proximal end to the distal end;
the sealing portion includes a first annular portion and a second annular portion;
the motion of the sealing portion relative to the instrument shaft includes axial motion relative to the axis of the instrument shaft, the axial motion being divided between opposite motions of the first annular portion and second annular portion; and
a first axial force applied to the instrument shaft by the first annular portion is substantially offset by a second axial force applied to the instrument shaft by the second annular portion.

43. The surgical system of claim 39, wherein the controller initiates or increases motion of the sealing portion of the actuated cannula seal when a velocity of displacement of the instrument shaft relative to the actuated cannula seal is below a threshold value.

44. The surgical system of claim 39, wherein the surgical system includes a filter configured to remove noise artifacts in signals received from the force sensor that are due to a vibratory excitation of the actuated cannula seal.

45. The surgical system of claim 39, wherein the cannula is coupled to the arm.

* * * * *